(12) United States Patent
Cundiff et al.

(10) Patent No.: US 12,035,927 B2
(45) Date of Patent: Jul. 16, 2024

(54) SURGICAL INSTRUMENTS INCLUDING A SET OF CUTTING BLADES FOR PERFORMING AN OSTEOTOMY

(71) Applicant: Fusion Orthopedics, LLC, Mesa, AZ (US)

(72) Inventors: Adam J. Cundiff, Mesa, AZ (US); Nathan G. Peterson, Mesa, AZ (US)

(73) Assignee: Fusion Orthopedics, LLC, Mesa, AZ (US)

( * ) Notice: Subject to any disclaimer, the term of this patent is extended or adjusted under 35 U.S.C. 154(b) by 322 days.

(21) Appl. No.: 17/538,781

(22) Filed: Nov. 30, 2021

(65) Prior Publication Data
US 2022/0079606 A1    Mar. 17, 2022

Related U.S. Application Data

(63) Continuation of application No. 16/537,495, filed on Aug. 9, 2019, now Pat. No. 11,253,273, which is a continuation-in-part of application No. 16/459,555, filed on Jul. 1, 2019, now Pat. No. 11,253,272.

(51) Int. Cl.
*A61B 17/16*    (2006.01)
(52) U.S. Cl.
CPC .............................. *A61B 17/1659* (2013.01)

(58) Field of Classification Search
CPC ... A61B 17/14; A61B 17/142; A61B 17/1659; A61B 17/151; A61B 17/152; B23D 3/00; B23D 61/006
See application file for complete search history.

(56) References Cited

U.S. PATENT DOCUMENTS

| 7,527,628 B2 * | 5/2009 | Fletcher ................ B27B 19/006 606/177 |
| 8,939,981 B1 * | 1/2015 | Anderson .............. A61B 17/14 606/82 |
| 10,159,499 B2 | 12/2018 | Dacosta et al. |
| 2018/0132868 A1 | 5/2018 | Dacosta et al. |

* cited by examiner

*Primary Examiner* — Andrew Yang

(57) ABSTRACT

Surgical instruments for performing wedge-shaped osteotomies are disclosed herein. One surgical instrument includes a body including a distal end, a proximal end, and a top surface. The top surface includes a slope extending upward and along a single plane from the distal end to the proximal end. Multiple columns of cutting blades positioned on the top surface and each of the cutting blades includes a respective uniform height that extends vertically along at least a portion of the slope. Another surgical instrument includes a top surface including a flat plane. Multiple columns of cutting blades are positioned on the top surface and the columns of cutting blades are spaced apart and positioned on at least a portion of the top surface. Each cutting blade extends horizontally along the top surface and includes an increasing slope extending upward and along a single plane from the distal end to the proximal end.

20 Claims, 13 Drawing Sheets

SURGICAL INSTRUMENTS INCLUDING A SET OF CUTTING BLADES FOR PERFORMING AN OSTEOTOMY

REFERENCE TO RELATED APPLICATION

This application is a Continuation of and claims priority to U.S. patent application Ser. No. 16/537,495, filed on Aug. 9, 2019, which is a Continuation-In-Part of and claims priority to U.S. patent application Ser. No. 16/459,555 filed on Jul. 1, 2019, the contents of each of which are incorporated herein by reference in their entirety.

FIELD OF THE TECHNOLOGY

The present technology relates generally to surgical cutting apparatus, and more particularly to, surgical instruments for performing osteotomies.

BACKGROUND

Surgical cutting instruments come in many shapes and sizes. Generally, osteotomy surgical instruments are designed to make straight cuts. In some situations, particularly when a wedge-shaped osteotomy is desired, the user (e.g., a physician, surgeon, etc.) is required to perform multiple osteotomies, cuts, and/or passes to achieve the desired shape. Further, multiple osteotomies with using a surgical instrument that make straight cuts can result in inconsistencies in shape and/or size of the resulting osteotomy wedges in different patients. In other words, it takes more time to perform a wedge-shaped osteotomy than is otherwise needed and/or there is a degree of inconsistency and/or inaccuracy when a traditional surgical instrument is utilized to perform a wedge-shaped osteotomy.

SUMMARY

Various embodiments provide a surgical instrument for performing an osteotomy. One surgical instrument includes a body including a distal end, a proximal end, a bottom surface, and a top surface. The top surface includes a slope extending upward and along a single plane from the distal end to the proximal end. The surgical instrument further includes multiple columns of cutting blades spaced apart on the top surface in which each of the cutting blades includes a respective uniform height and extend vertically along at least a portion of the slope from the distal end to the proximal end.

Another surgical instrument includes a body including a distal end, a proximal end, a bottom surface, and a top surface including a flat plane. The surgical instrument further includes multiple columns of cutting blades positioned on the top surface in which the columns of cutting blades are spaced apart and positioned on the top surface from the distal end to the proximal end. Each cutting blade extends horizontally along the top surface and includes an increasing slope extending upward and along a single plane from the distal end to the proximal end.

BRIEF DESCRIPTION OF THE DRAWINGS

To readily understand the advantages and benefits of the technology, a more particular description of the technology briefly described above will be rendered by reference to specific embodiments that are illustrated in the appended drawings. Understanding that these drawings depict typical embodiments of the technology, and are therefore not to be considered to be limiting of its scope, the technology will be described and explained with additional specificity and detail through the use of the accompanying drawings, in which.

DETAILED DESCRIPTION OF THE DRAWINGS

Figure 1A:
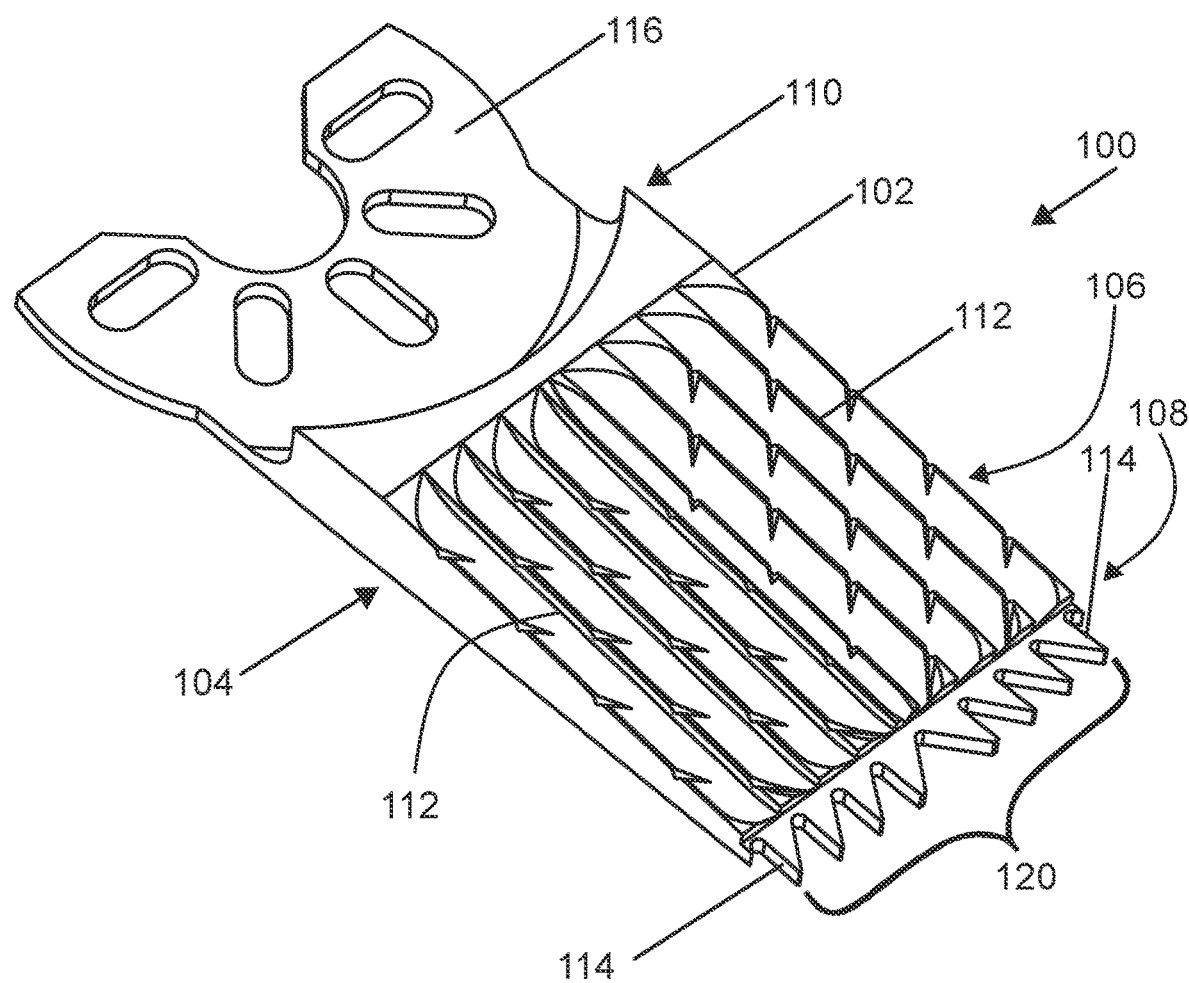
FIG. 1A is a schematic diagram illustrating an overall view of an embodiment of a surgical instrument including multiple columns of cutting blades.
Figure 1B:
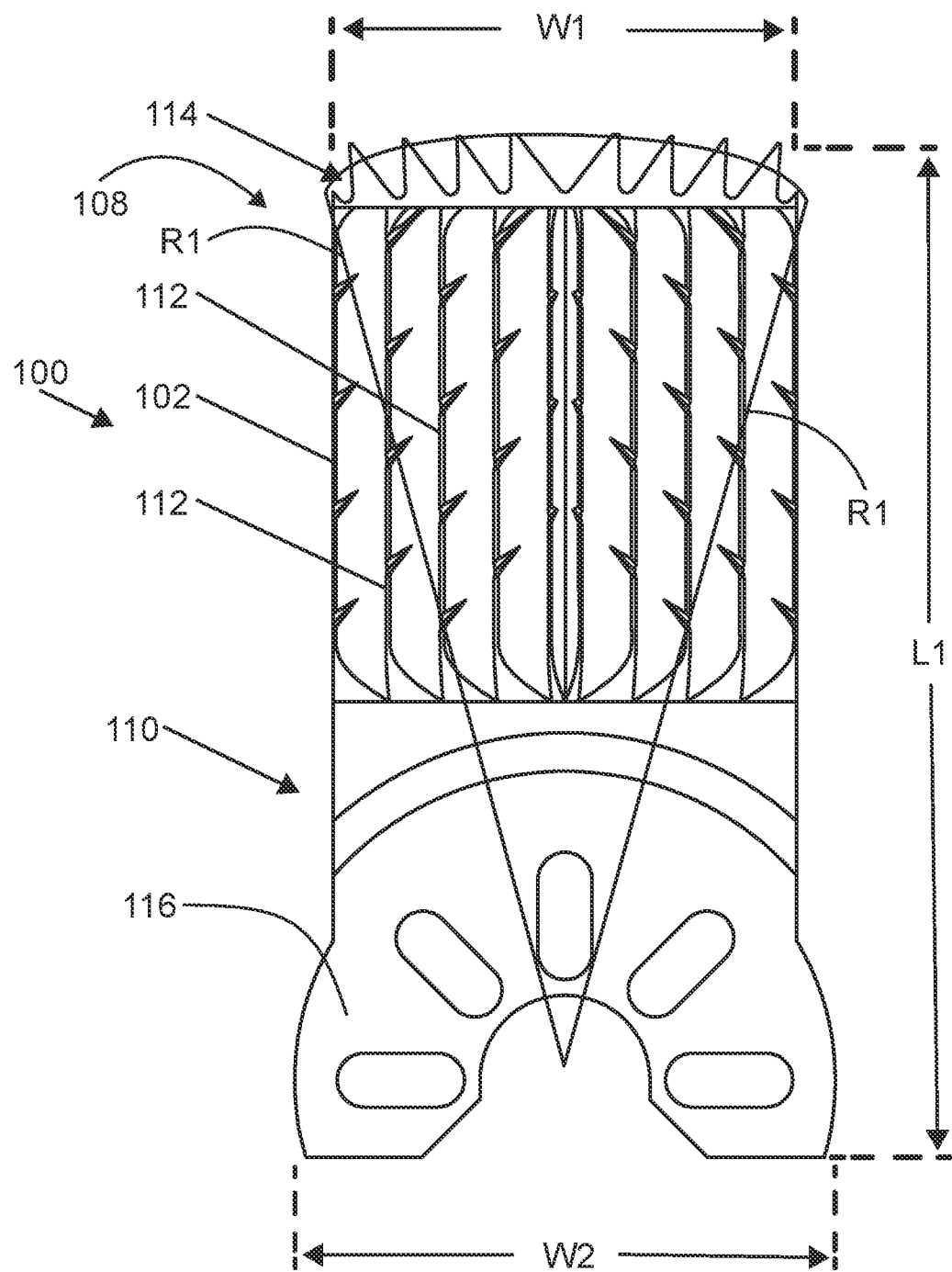
FIG. 1B is a schematic diagram illustrating a top view of the embodiment of a surgical instrument illustrated in FIG. 1A.

It should be understood that the language used in the present disclosure has been principally selected for readability and instructional purposes, and not to limit the scope of the subject matter disclosed herein in any manner. Further, reference throughout this specification to "one embodiment," "an embodiment," or similar language means that a particular feature, structure, or characteristic described in connection with the embodiment is included in at least one embodiment. Thus, appearances of the phrases "in one embodiment," "in an embodiment," and similar language throughout this specification may, but do not necessarily, all refer to the same embodiment, but mean "one or more but not all embodiments" unless expressly specified otherwise. The terms "including," "comprising," "having," and variations thereof mean "including, but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise.

In addition, as used herein, the term "set" can mean "one or more," unless expressly specified otherwise. The term "sets" can mean multiples of or a plurality of "one or mores," "ones or more," and/or "ones or mores" consistent with set theory, unless expressly specified otherwise.

Furthermore, the described features, advantages, and characteristics of the embodiments may be combined in any suitable manner. One skilled in the relevant art will recognize that the embodiments may be practiced without one or more of the specific features or advantages of a particular embodiment. In other instances, additional features and advantages may be recognized in certain embodiments that may not be present in all embodiments.

The present technology may include any type of surgical instrument and is not limited to the style of surgical instrument depicted in the drawings. Furthermore, the described features, structures, or characteristics of the various embodiments may be combined in any suitable manner. One skilled in the relevant art will recognize, however, that embodiments may be practiced without one or more of the specific details, or with other methods, components, materials, and so forth. In other instances, well-known structures, and/or materials are not shown or described in detail to avoid obscuring aspects of an embodiment.

Turning now to the Figures, FIGS. 1A through 1D are schematic diagrams illustrating various views of one embodiment of a surgical instrument 100. In various embodiments, the surgical instrument 100 can be utilized to perform a wedge-shaped osteotomy. Further, the wedge-shaped osteotomy can be achieved with a single cut or pass utilizing the surgical instrument 100.

A surgical instrument 100 may be constructed of any suitable material that can cut bone. In various embodiments, the surgical instrument 100 is constructed of a sterilized suitable material that can cut bone. In some embodiments, the surgical instrument 100 includes stainless steel, among other suitable materials that are possible and contemplated herein. In additional or alternative embodiments, the surgical instrument 100 includes surgical grade stainless steel, among other suitable surgical grade materials that are possible and contemplated herein.

At least in the illustrated embodiment, the surgical instrument 100 includes, among other features, a body 102 including at least a bottom surface 104, a top surface 106, a distal end 108, and a proximal end 110, a set of cutting blades 112 positioned on the body 102, a set of cutting teeth 114 positioned on the distal end 108, and an attachment mechanism 116 positioned on the proximal end 110. A body 102 may include any suitable dimensions that can perform an osteotomy. In various embodiments, the body 102 includes dimensions that are suitable for performing an osteotomy on a human.

In various embodiments, the body 102 includes a length L1 (see FIG. 1B) in the range of about 15 mm to about 70 mm, among other ranges of length and/or lengths that are possible and contemplated herein. In some embodiments, the body 102 includes a length L1 of about 20 mm, among other lengths that are possible and contemplated herein.

The body 102 further includes a width W1 (see FIG. 1B) at the distal end 108 and a width W2 (see FIG. 1B) at the proximal end 110. In various embodiments, the width W1 is in the range of about 5 mm to about 30 mm, among other ranges of widths and/or widths that are possible and contemplated herein. In some embodiments, the width W1 is about 7.5 mm, among other widths that are possible and contemplated herein. In additional or alternative embodiments, the width W2 is in the range of about 5 mm to about 70 mm, among other ranges of widths and/or widths that are possible and contemplated herein. In some embodiments, the width W2 is about 11 mm, among other widths that are possible and contemplated herein.

In some embodiments, the width W1 and the width W2 are the same width or substantially the same width. In other embodiments, the width W2 is greater than the width W1 such that the proximate end 110 is wider than the distal end 108 or, alternatively, the distal end 108 is narrower than the proximate end 110 (e.g., the width W1 is less than the width W2). That is, in various embodiments, the surgical instrument 100 includes a tapered shape and/or tapers from the distal end 108 to the proximate end 110.

A bottom surface 104 may include any suitable shape and/or profile that can facilitate or assist the surgical instrument 100 in performing an osteotomy (e.g., a wedge-shaped osteotomy). In various embodiments, the bottom surface 104 includes a flat or substantially flat surface, among other profiles and/or planes that are possible and contemplated herein.

A top surface 106 may include any suitable profile upon which one or more cutting blades 112 can be positioned. In various embodiments, the top surface 106 includes a slope 118 (see FIGS. 1C and 1D) that extends upward and/or away from the bottom surface 104 and the distal end 108. The slope 118 may include any suitable grade (e.g., rise over run) that can facilitate and/or assist the surgical instrument 100 in performing an osteotomy and particularly, a wedge-shaped osteotomy. That is, the top surface 106 and/or surgical instrument 100 may include any suitable grade that can facilitate and/or assist the surgical instrument 100 in performing a wedge-shaped osteotomy in one cut and/or one pass.

Figure 1C:
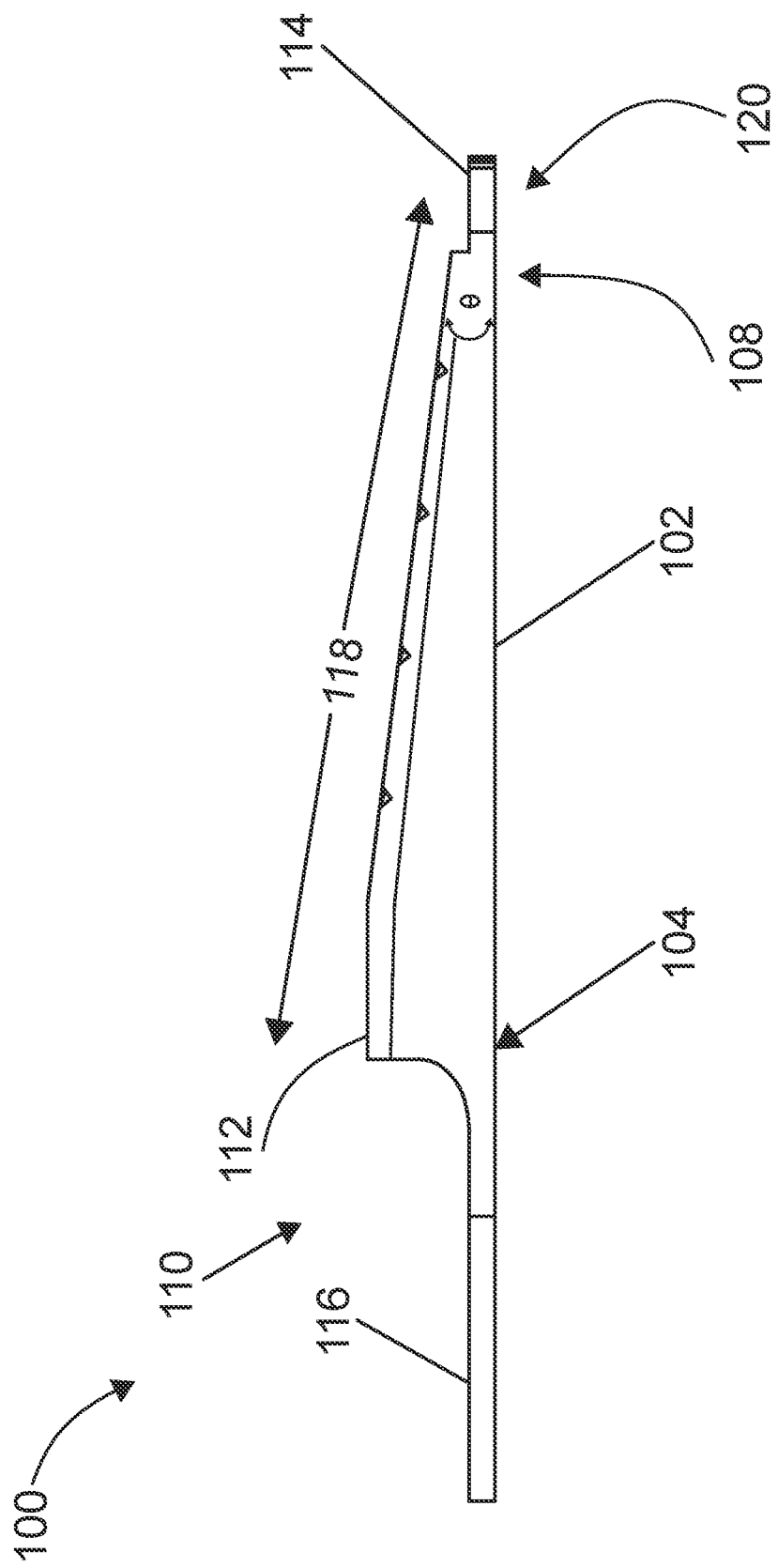
FIG. 1C is a schematic diagram illustrating a side view of the embodiment of a surgical instrument illustrated in FIG. 1A.
Figure 1D:
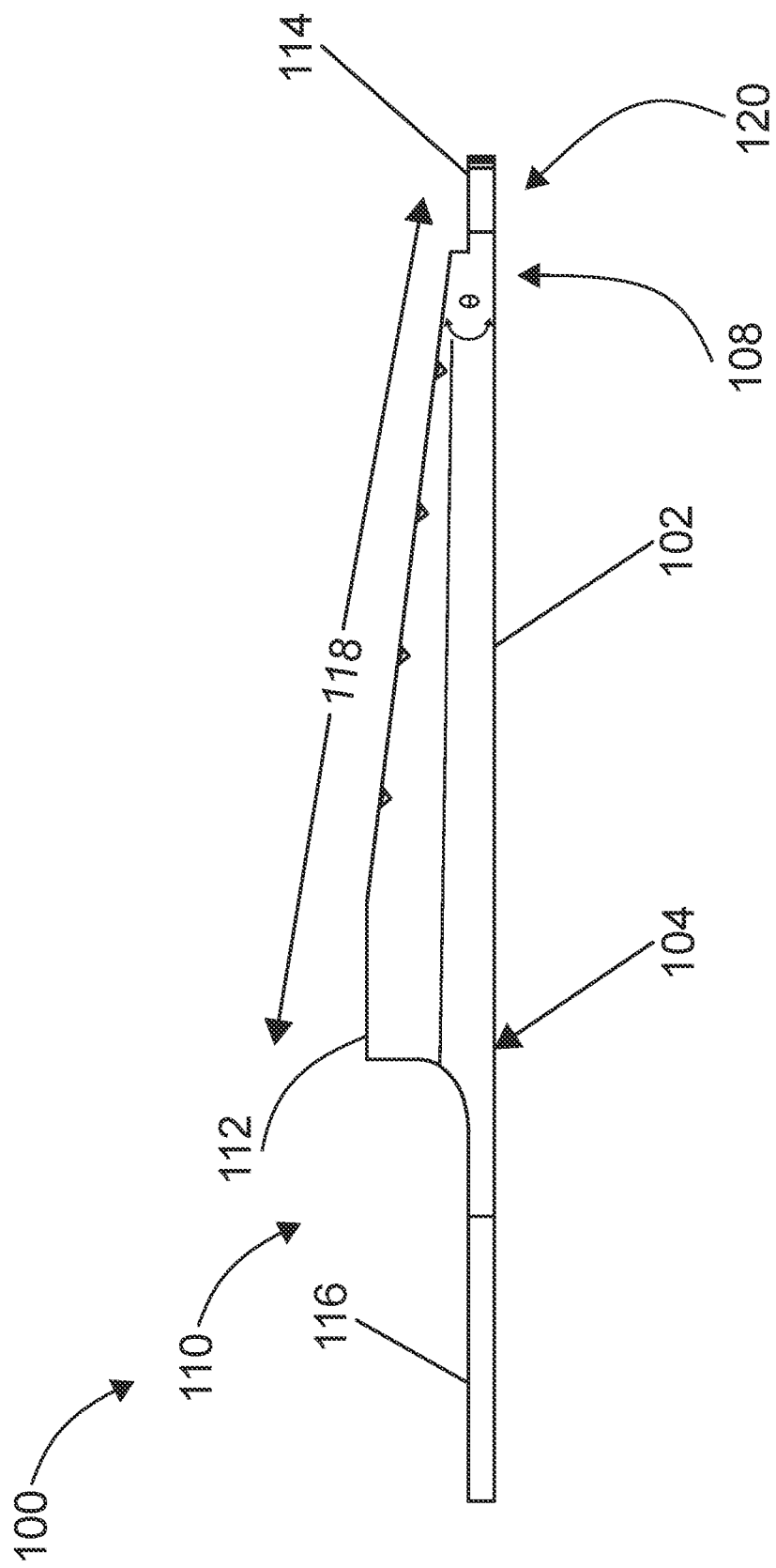
FIG. 1D is a schematic diagram illustrating a side view of the embodiment of a surgical instrument illustrated in FIG. 1A with gradually increasing blade heights.

In various embodiments, the slope 118 includes a grade in the range of about zero degrees (0° or flat) to about fifteen degrees (15°), among other ranges of grades, grades, and/or slopes that are possible and contemplated herein. In other words, an angle $\theta$ in the range of about 0° to about 15° (e.g., the angle $\theta = 0°$, 1°, 2°, 3°, 4°, 5°, 6°, 7°, 8°, 9°, 10°, 11°, 12°, 13°, 14°, or 15° and/or the angle $\theta \approx 0°$, 1°, 2°, 3°, 4°, 5°, 6°, 7°, 8°, 9°, 10°, 11°, 12°, 13°, 14°, or 15°) is defined between the top surface 106 and the bottom surface 104 beginning at the distal end 108 and extending upward and toward the proximate end 110, as shown in FIGS. 1C and 1D. In some embodiments, the slope 118 includes a grade of about seven (7°) degrees (e.g., the angle $\theta = 7°$ or the angle $\theta \approx 7°$), among other suitable grades and/or slopes that are possible and contemplated herein.

In several embodiments, the top surface 106 includes a set of cutting blades 112 positioned thereon. As illustrated, the set of cutting blades 112 are spaced apart and positioned vertically to form a set of columns of cutting blades 112.

A set of cutting blades 112 may include any suitable quantity of cutting blades 112 and/or quantity of columns of cutting blades 112 that can facilitate and/or assist the surgical instrument 100 in performing an osteotomy and particularly, a wedge-shaped osteotomy. In various embodiments, the top surface 106 includes a suitable quantity of cutting blades 112 so that the surgical instrument 100 can perform a wedge-shaped osteotomy in one cut and/or one pass.

In various embodiments, the top surface 106 includes a quantity of cutting blades 112 in the range of about 2 cutting blades 112 to about 40 cutting blades 112, among other ranges of quantities of cutting blades 112 and/or quantities of cutting blades 112 that are possible and contemplated herein. In some embodiments, the top surface 106 includes 12 cutting blades 112, among other quantities of cutting blades 112 that are possible and contemplated herein.

While the surgical instrument 100 is shown with a top surface 106 including 8 cutting blades 112, the various embodiments of the surgical instrument 100 are not limited to 8 cutting blades 112. That is, various other embodiments of a surgical instrument 100 can include a different quantity of cutting blades 112 such that the top surface 106 can include a greater quantity of cutting blades 112 than 8 cutting blades 112 or a smaller quantity of cutting blades 112 than 8 cutting blades 112.

In some embodiments, the cutting blades 112 may be included on the entirety or substantially the entirety of the top surface 106. In other embodiments, the cutting blades 112 may be included on a portion or at least a portion of the top surface 106. That is, the cutting blades 112 may extend partially or fully from the distal end 108 to the proximal end 110.

The portion of the top surface 106 including the cutting blades 112 may include any suitable sized portion that can produce a wedge-shaped osteotomy. Various embodiments of the surgical instrument 100 may include varying sized portions of the top surface 106 including the cutting blades 112 so that different sized and/or wedge-shaped osteotomies can be obtained. That is, different embodiments may include cutting blades 112 with differing lengths to produce different sized and/or wedge-shaped osteotomies.

A cutting blade 112 may include any suitable shape that can facilitate and/or assist the surgical instrument 100 in performing an osteotomy (e.g., a wedge-shaped osteotomy). In various embodiments, a cutting blade 112 can include a curved blade (e.g., a vertically curved blade), a straight blade, waved blade (e.g., a horizontally curved blade), or a wavy blade (e.g., a blade with multiple horizontal curves), among other suitable shapes that can facilitate cutting bone that are possible and contemplated herein. In additional or alternative embodiments, a cutting blade 112 can include a straight cutting edge and/or a serrated cutting edge, among other cutting edges that are possible and contemplated herein.

In some embodiments, all of the cutting blades 112 in the set of cutting blades 112 on the top surface 106 include the same or substantially the same shape. In alternative embodiments, at least two cutting blades 112 in the set of cutting blades 112 on the top surface 106 include different shapes or substantially different shapes. In one non-limiting example, at least one cutting blade 112 includes a straight blade and at least one cutting blade 112 includes a curved blade (or other non-straight blade), among other shapes and/or combinations of shapes that are possible and contemplated herein. In an additional or alternative non-limiting example, the straight blade(s) and/or the curved blade(s) include a serrated cutting edge.

In additional or alternative embodiments, a set of cutting blades 112 can include at least two subsets of cutting blades 112 in which a first subset includes two or more cutting blades 112 including a first shape and at least a second subset that includes two or more cutting blades 112 including a second, different shape. In some embodiments, one or more of the cutting blades 112 in one or more of the subsets of cutting blades 112 includes a serrated edge.

In further additional or alternative embodiments, the first subset of cutting blades 112 and the second subset of cutting blades 112 include the same quantity of cutting blades 112. In other embodiments, the first subset of cutting blades 112 and the second subset of cutting blades 112 include different quantities of cutting blades 112.

In yet further additional or alternative embodiments, the cutting blades 112 in the first subset of cutting blades 112 and the cutting blades 112 in the second subset of cutting blades 112 can be positioned in a pattern. The pattern may include any suitable pattern that can assist in and/or facilitate performing an osteotomy (e.g., a wedge-shaped osteotomy). In some embodiments, the pattern may include cutting blades 112 with different shapes in an alternating pattern to provide alternating columns of cutting blades 112.

A cutting blade 112 may include any suitable height that can facilitate and/or assist the surgical instrument 100 in performing an osteotomy (e.g., a wedge-shaped osteotomy). In various embodiments, the cutting blades 112 can include a height in the range of about 0.1 mm to about 30 mm, among other suitable heights that can facilitate cutting bone that are possible and contemplated herein. In some embodiments, the cutting blades 112 include a height of 0.75 mm.

In some embodiments, all of the cutting blades 112 in the set of cutting blades 112 on the top surface 106 include a uniform height (see FIG. 1C). In alternative embodiments, one or more of the cutting blades 112 on the top surface 106 include a height that gradually increases from the distal end 108 to the proximal end 110 (see FIG. 1D).

As shown, the distal end 108 includes a set of cutting teeth 114 (e.g., a single tooth 114 or multiple teeth 114) positioned thereon. A set of cutting teeth 114 may include any suitable quantity of teeth 114 that can assist in and/or facilitate initiating an osteotomy and particularly, a wedge-shaped osteotomy, when oscillated.

In various embodiments, the set of cutting teeth 114 includes a quantity of cutting teeth 114 in the range of one (1) cutting tooth 114 to about 50 cutting teeth 114, among other ranges of quantities and/or quantities of cutting teeth 114 that are possible and contemplated herein. In some embodiments, a set of cutting teeth 114 includes about 8 cutting teeth 114, among other quantities of cutting teeth 114 that are possible and contemplated herein.

In some embodiments, the set of cutting teeth 114 are positioned on the distal end 108 in a straight line or substantially straight line. In other embodiments, the set of cutting teeth 114 are positioned along a curve on the distal end 108 defined by a radius R1.

The radius R1 may be any suitable radius and/or curvature that can assist in and/or facilitate initiating an osteotomy (e.g., a wedge-shaped osteotomy) when oscillated. In various embodiments, the radius R1 is in the range of about 5 mm to about 80 mm, among other ranges of lengths and/or lengths that can define an amount and/or degree of curvature that are possible and contemplated herein. In some embodiments, the radius R1 is about 25 mm, among other lengths that can define an amount and/or degree of curvature that are possible and contemplated herein.

In some embodiments, the set of cutting teeth 114 on the distal end 108 may define a cutting tip 120 that can initiate an osteotomy (e.g., a wedge osteotomy). Further, the cutting blades 112 positioned along the single-plane slope 118 may define a cutting slope 118 that can perform the osteotomy to produce a wedge-shaped cut. In various embodiments, the coordination of the cutting tip 120 and the cutting slope 118 can allow the surgical instrument 100 to produce a wedge-shaped osteotomy in a single cut and/or single pass.

As further shown, the proximal end 110 includes an attachment mechanism 116 positioned thereon. The attachment mechanism 116 may include any suitable size dimensions, shape, and/or configuration that enables attachments of the surgical instrument 100 to a surgical instrument (not shown). That is, while the attachment mechanism 116 is shown as including particular relative size dimensions, shapes, and configurations, the various embodiments of the surgical instrument 100 are not limited to the illustrated attachment mechanism 116. That is, other embodiments of the surgical instrument 100 may include one or more different relative size dimension(s), shapes, and/or configurations.

FIGS. 2A through 2D are schematic diagrams illustrating various views of another embodiment of a surgical instrument 200. In various embodiments, the surgical instrument 200 can be utilized to perform a wedge-shaped osteotomy. Further, the wedge-shaped osteotomy can be achieved with a single cut or pass utilizing the surgical instrument 200.

A surgical instrument 200 may be constructed of any suitable material that can cut bone. In various embodiments, the surgical instrument 200 is constructed of a sterilized suitable material that can cut bone. In some embodiments, the surgical instrument 200 includes stainless steel, among other suitable materials that are possible and contemplated herein. In additional or alternative embodiments, the surgical instrument 200 includes surgical grade stainless steel, among other suitable surgical grade materials that are possible and contemplated herein.

At least in the illustrated embodiment, the surgical instrument 200 includes, among other features, a body 202 including at least a bottom surface 204, a top surface 206, a distal end 208, and a proximal end 210, a set of cutting blades 212 positioned on the body 202, a set of cutting teeth 214 positioned on the distal end 208, and an attachment mechanism 216 positioned on the proximal end 210. A body 202 may include any suitable dimensions that can perform an osteotomy. In various embodiments, the body 202 includes dimensions that are suitable for performing an osteotomy on a human.

In various embodiments, the body 202 includes a length L2 (see FIG. 2B) in the range of about 15 mm to about 70 mm, among other ranges of length and/or lengths that are possible and contemplated herein. In some embodiments, the body 202 includes a length L2 of about 20 mm, among other lengths that are possible and contemplated herein.

The body 202 further includes a width W3 (see FIG. 2B) at the distal end 208 and a width W4 (see FIG. 2B) at the proximal end 210. In various embodiments, the width W3 is in the range of about 5 mm to about 30 mm, among other ranges of widths and/or widths that are possible and contemplated herein. In some embodiments, the width W3 is about 7.5 mm, among other widths that are possible and contemplated herein. In additional or alternative embodiments, the width W4 is in the range of about 5 mm to about 70 mm, among other ranges of widths and/or widths that are possible and contemplated herein. In some embodiments, the width W4 is about 11 mm, among other widths that are possible and contemplated herein.

In some embodiments, the width W3 and the width W4 are the same width or substantially the same width. In other embodiments, the width W4 is greater than the width W3 such that the proximate end 210 is wider than the distal end 208 or, alternatively, the distal end 208 is narrower than the proximate end 210 (e.g., the width W3 is less than the width W4). That is, in various embodiments, the surgical instrument 200 includes a tapered shape and/or tapers from the distal end 208 to the proximate end 210.

A bottom surface 204 may include any suitable shape and/or profile that can facilitate or assist the surgical instrument 200 in performing an osteotomy (e.g., a wedge-shaped osteotomy). In various embodiments, the bottom surface 204 includes a flat or substantially flat surface, among other profiles and/or planes that are possible and contemplated herein.

A top surface 206 may include any suitable profile upon which one or more cutting blades 212 can be positioned. In various embodiments, the top surface 206 includes a slope 218 (see FIGS. 2C and 2D) that extends upward and/or away from the bottom surface 204 and the distal end 208. The slope 218 may include any suitable grade (e.g., rise over run) that can facilitate and/or assist the surgical instrument 200 in performing an osteotomy and particularly, a wedge-shaped osteotomy. That is, the top surface 206 and/or surgical instrument 200 may include any suitable grade that can facilitate and/or assist the surgical instrument 200 in performing a wedge-shaped osteotomy in one cut and/or one pass.

Figure 2A:
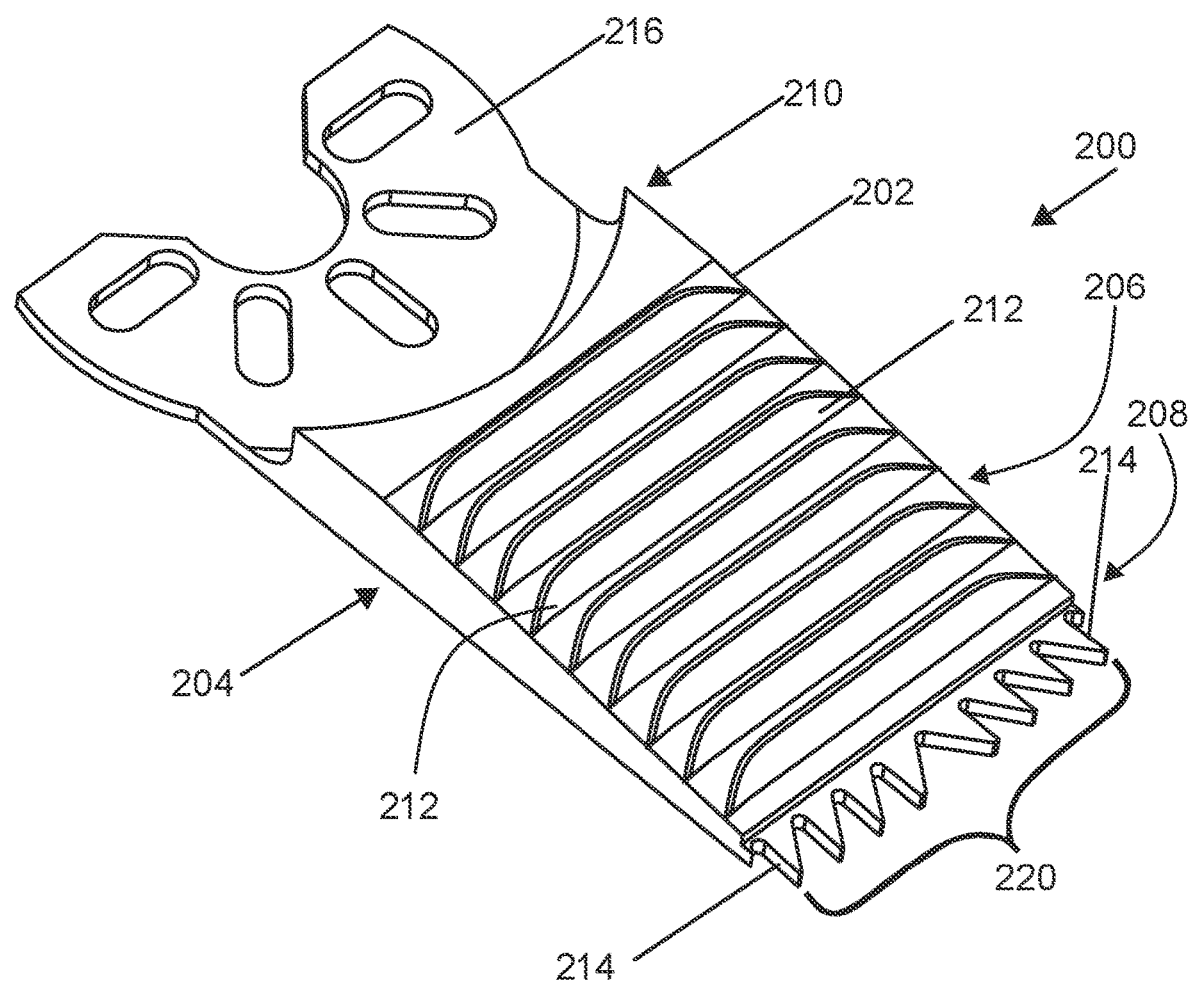
FIG. 2A is a schematic diagram illustrating an overall view of an embodiment of a surgical instrument including multiple rows of cutting blades.
Figure 2B:
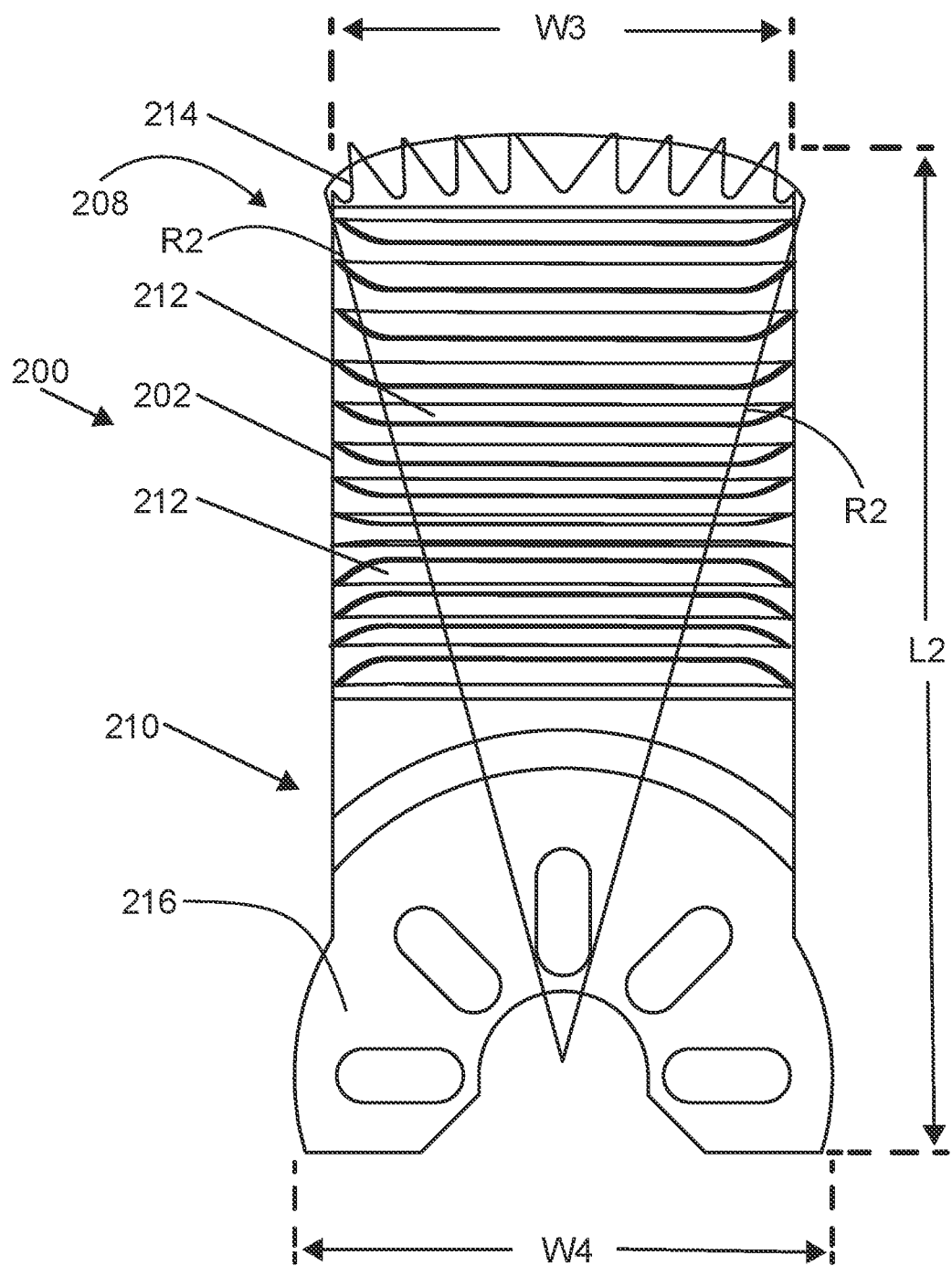
FIG. 2B is a schematic diagram illustrating a top view of the embodiment of a surgical instrument illustrated in FIG. 2A.
Figure 2C:
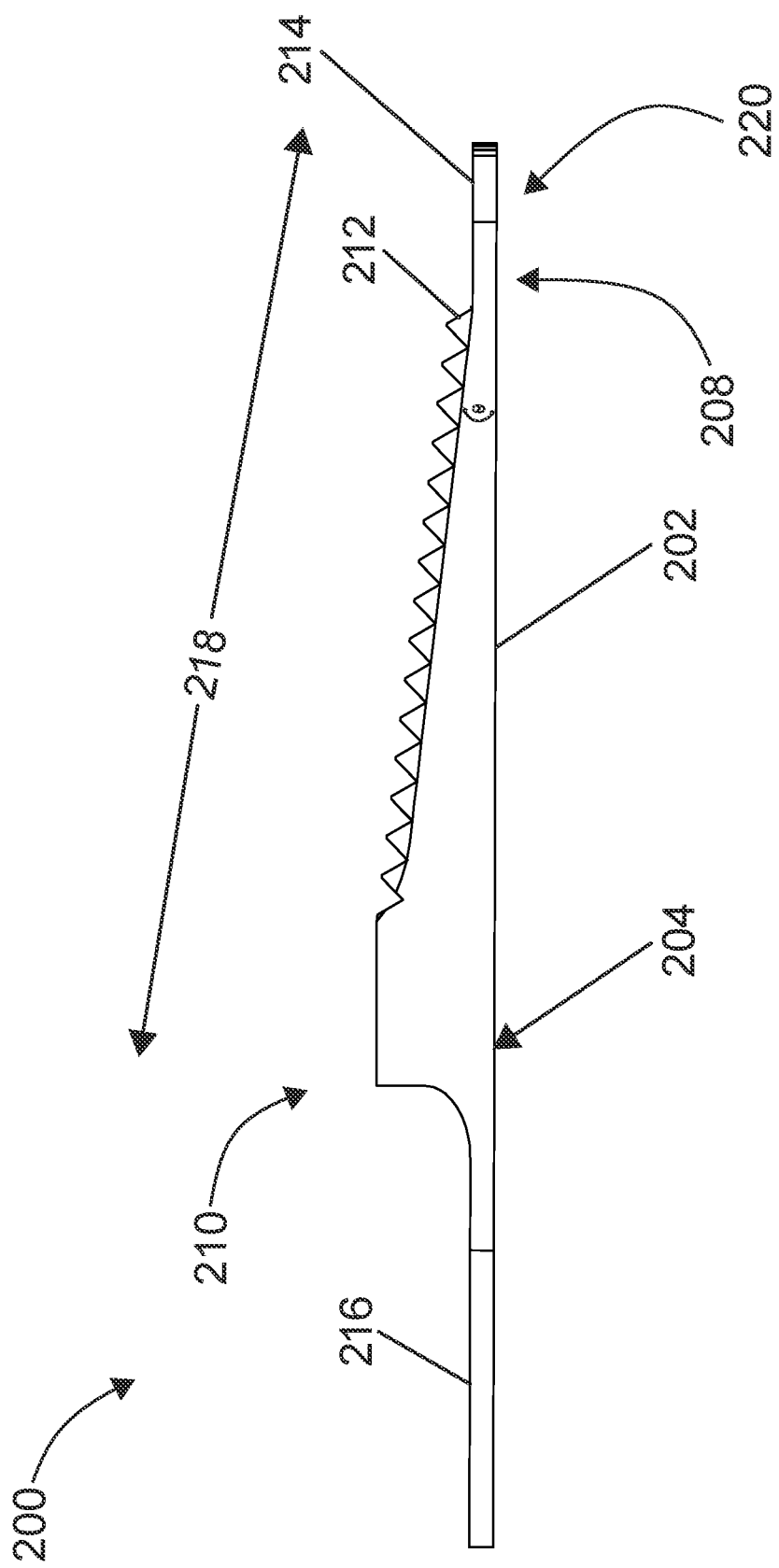
FIG. 2C is a schematic diagram illustrating a side view of the embodiment of a surgical instrument illustrated in FIG. 2A.
Figure 2D:
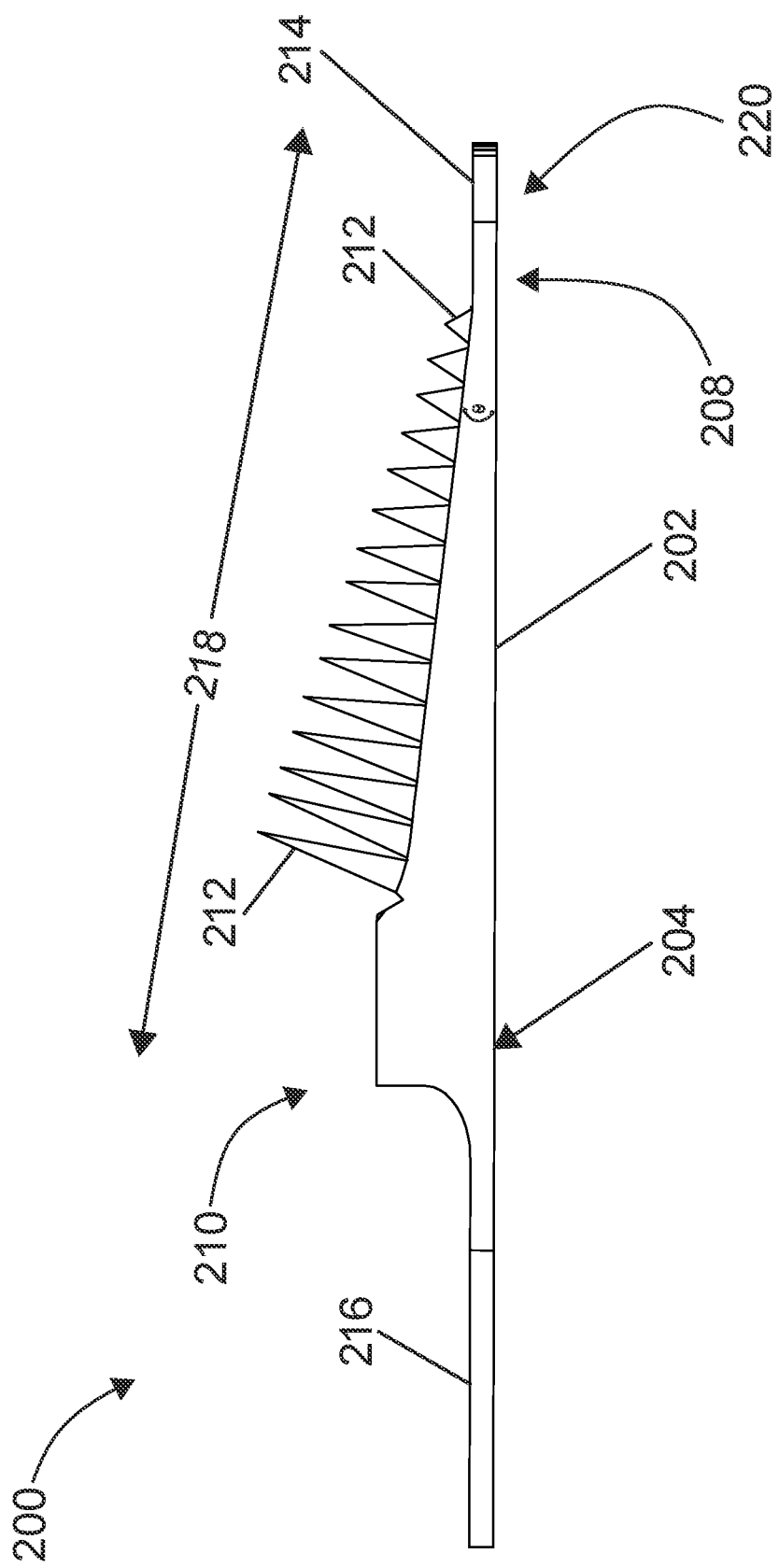
FIG. 2D is a schematic diagram illustrating a side view of the embodiment of a surgical instrument illustrated in FIG. 2A with each row including a gradually greater blade height from a distal end to a proximal end of the surgical instrument.

In various embodiments, the slope 218 includes a grade in the range of about 0° (or flat) to about 15°, among other ranges of grades, grades, and/or slopes that are possible and contemplated herein. In other words, an angle $\theta$ in the range of about 0° to about 15° (e.g., the angle $\theta$=0°, 1°, 2°, 3°, 4°, 5°, 6°, 7°, 8°, 9°, 10°, 11°, 12°, 13°, 14°, or 15° and/or the angle $\theta \approx$0°, 1°, 2°, 3°, 4°, 5°, 6°, 7°, 8°, 9°, 10°, 11°, 12°, 13°, 14°, or 15°) is defined between the top surface 206 and the bottom surface 204 beginning at the distal end 208 and extending upward and toward the proximate end 210, as shown in FIGS. 2C and 2D. In some embodiments, the slope 218 includes a grade of about 7° degrees (e.g., the angle $\theta$=7° or the angle $\theta \approx$7°), among other suitable grades and/or slopes that are possible and contemplated herein.

In several embodiments, the top surface 206 includes a set of cutting blades 212 positioned thereon. As illustrated, the set of cutting blades 212 are spaced apart and positioned horizontally to form a set of rows of cutting blades 212.

A set of cutting blades 212 may include any suitable quantity of cutting blades 212 and/or quantity of rows of cutting blades 212 that can facilitate and/or assist the surgical instrument 200 in performing an osteotomy and particularly, a wedge-shaped osteotomy. In various embodiments, the top surface 206 includes a suitable quantity of cutting blades 212 or rows of cutting blades 212 so that the surgical instrument 200 can perform a wedge-shaped osteotomy in one cut and/or one pass.

In various embodiments, the top surface 206 includes a quantity of cutting blades 212 in the range of about two (2) cutting blades 212 to about 40 cutting blades 212, among other ranges of quantities of cutting blades 212 and/or quantities of cutting blades 212 that are possible and contemplated herein. In some embodiments, the top surface 206 includes 12 cutting blades 212, among other quantities of cutting blades 212 that are possible and contemplated herein.

While the surgical instrument 200 is shown with a top surface 206 including 9 cutting blades 212, the various embodiments of the surgical instrument 200 are not limited to 9 cutting blades 212. That is, various other embodiments of a surgical instrument 200 can include a different quantity of cutting blades 212 such that the top surface 206 can include a greater quantity of cutting blades 212 than 9 cutting blades 212 or a smaller quantity of cutting blades 212 than 9 cutting blades 212.

In some embodiments, the cutting blades 212 may be included on the entirety or substantially the entirety of the top surface 206. In other embodiments, the cutting blades 212 may be included on a portion or at least a portion of the top surface 206. That is, the quantity of rows of cutting blades 212 may extend partially or fully along the slope 208 on the top surface 106.

The portion of the top surface 206 including the cutting blades 212 may include any suitable sized portion that can produce a wedge-shaped osteotomy. Various embodiments of the surgical instrument 200 may include varying sized portions of the top surface 206 including the cutting blades 212 so that different sized and/or shaped wedge-shaped osteotomies can be obtained.

A cutting blade 212 may include any suitable shape that can facilitate and/or assist the surgical instrument 200 in performing an osteotomy (e.g., a wedge-shaped osteotomy). In various embodiments, a cutting blade 212 can include a curved blade, a straight blade, waved blade, or a wavy blade, among other suitable shapes that can facilitate cutting bone that are possible and contemplated herein. In additional or alternative embodiments, a cutting blade 212 can include a straight cutting edge and/or a serrated cutting edge, among other cutting edges that are possible and contemplated herein.

In some embodiments, all of the cutting blades 212 in the set of cutting blades 212 on the top surface 206 include the same or substantially the same shape. In alternative embodiments, at least two cutting blades 212 in the set of cutting blades 212 on the top surface 206 include different shapes or substantially different shapes. In one non-limiting example, at least one cutting blade 212 includes a straight blade and at least one cutting blade 212 includes a non-straight blade, among other shapes and/or combinations of shapes that are possible and contemplated herein. In an additional or alternative non-limiting example, the curved blade(s) and/or the straight blade(s) include a serrated edge.

In additional or alternative embodiments, a set of cutting blades 212 can include at least two subsets of cutting blades 212 in which a first subset includes two or more cutting blades 212 including a first shape and at least a second subset that includes two or more cutting blades 212 including a second, different shape. In some embodiments, one or more of the cutting blades 212 in one or more of the subsets of cutting blades 212 include a serrated edge.

In further additional or alternative embodiments, the first subset of cutting blades 212 and the second subset of cutting blades 212 include the same quantity of cutting blades 212. In other embodiments, the first subset of cutting blades 212 and the second subset of cutting blades 212 include different quantities of cutting blades 212.

In yet further additional or alternative embodiments, the cutting blades 212 in the first subset of cutting blades 212 and the cutting blades 212 in the second subset of cutting blades 212 can be positioned in a pattern. The pattern may include any suitable pattern that can assist in and/or facilitate performing an osteotomy (e.g., a wedge-shaped osteotomy). In some embodiments, the pattern may include cutting blades 212 with different shapes in an alternating pattern to provide alternating rows of cutting blades 212.

A cutting blade 212 may include any suitable height that can facilitate and/or assist the surgical instrument 200 in performing an osteotomy (e.g., a wedge-shaped osteotomy). In various embodiments, the cutting blades 212 can include a height in the range of about 0.1 mm to about 30 mm, among other suitable heights that can facilitate cutting bone that are possible and contemplated herein. In some embodiments, the cutting blades 212 include a height of 0.75 mm.

In some embodiments, all of the rows of cutting blades 212 on the top surface 206 include a uniform height (see FIG. 2C). In alternative embodiments, the rows of cutting blades 212 on the top surface 206 include a gradually increasing height (see FIG. 2D). In some embodiments, the height of the rows of cutting blades 212 gradually increases from the distal end 208 to the proximal end 210.

As shown, the distal end 208 includes a set of cutting teeth 214 (e.g., a single tooth 214 or multiple teeth 214) positioned thereon. A set of cutting teeth 214 may include any suitable quantity of teeth 214 that can assist in and/or facilitate initiating an osteotomy and particularly, a wedge-shaped osteotomy, when oscillated.

In various embodiments, the set of cutting teeth 214 includes a quantity of cutting teeth 214 in the range of one cutting tooth 214 to about 50 cutting teeth 214, among other ranges of quantities and/or quantities of cutting teeth 214 that are possible and contemplated herein. In some embodiments, a set of cutting teeth 214 includes about 8 cutting teeth 214, among other quantities of cutting teeth 214 that are possible and contemplated herein.

In some embodiments, the set of cutting teeth 214 are positioned on the distal end 208 in a straight line or substantially straight line. In other embodiments, the set of cutting teeth 214 are positioned along a curve on the distal end 208 defined by a radius R2.

The radius R2 may be any suitable radius and/or curvature that can assist in and/or facilitate initiating an osteotomy (e.g., a wedge-shaped osteotomy) when oscillated. In various embodiments, the radius R2 is in the range of about 5 mm to about 80 mm, among other ranges of lengths and/or lengths that can define an amount and/or degree of curvature that are possible and contemplated herein. In some embodiments, the radius R2 is about 25 mm, among other lengths that can define an amount and/or degree of curvature that are possible and contemplated herein.

In some embodiments, the set of cutting teeth 214 on the distal end may define a cutting tip 220 that can initiate an osteotomy (e.g., a wedge osteotomy). Further, the cutting blades 212 positioned along the single-plane slope 218 may define a cutting slope 218 that can perform the osteotomy to produce a wedge-shaped cut. In various embodiments, the coordination of the cutting tip 220 and the cutting slope 218 can allow the surgical instrument 200 to produce a wedge-shaped osteotomy in a single cut and/or single pass.

As further shown, the proximal end 210 includes an attachment mechanism 216 positioned thereon. The attachment mechanism 216 may include any suitable size dimensions, shape, and/or configuration that enables attachments of the surgical instrument 200 to a surgical instrument (not shown). That is, while the attachment mechanism 216 is shown as including particular relative size dimensions, shapes, and configurations, the various embodiments of the surgical instrument 200 are not limited to the illustrated attachment mechanism 216. That is, other embodiments of the surgical instrument 200 may include one or more different relative size dimension(s), shapes, and/or configurations.

With reference to FIGS. 3A through 3E, FIGS. 3A through 3E are schematic diagrams illustrating various views of one embodiment of a surgical instrument 300. In various embodiments, the surgical instrument 300 can be utilized to perform a wedge-shaped osteotomy. Further, the wedge-shaped osteotomy can be achieved with a single cut or pass utilizing the surgical instrument 300.

A surgical instrument 300 may be constructed of any suitable material that can cut bone. In various embodiments, the surgical instrument 300 is constructed of a sterilized suitable material that can cut bone. In some embodiments, the surgical instrument 300 includes stainless steel, among other suitable materials that are possible and contemplated herein. In additional or alternative embodiments, the surgical instrument 300 includes surgical grade stainless steel, among other suitable surgical grade materials that are possible and contemplated herein.

At least in the illustrated embodiment, the surgical instrument 300 includes, among other features, a body 302 including at least a bottom surface 304, a top surface 306, a distal end 308, and a proximal end 310, a set of cutting blades 312 positioned on the body 302, a set of cutting teeth 314 positioned on the distal end 308, and an attachment mechanism 316 positioned on the proximal end 310. A body 302 may include any suitable dimensions that can perform an osteotomy. In various embodiments, the body 302 includes dimensions that are suitable for performing an osteotomy on a human.

In various embodiments, the body 302 includes a length L3 (see FIG. 3B) in the range of about 15 mm to about 70 mm, among other ranges of length and/or lengths that are possible and contemplated herein. In some embodiments, the body 302 includes a length L3 of about 20 mm, among other lengths that are possible and contemplated herein.

The body 302 further includes a width W5 (see FIG. 3B) at the distal end 308 and a width W6 (see FIG. 3B) at the proximal end 310. In various embodiments, the width W5 is in the range of about 5 mm to about 30 mm, among other ranges of widths and/or widths that are possible and contemplated herein. In some embodiments, the width W5 is about 7.5 mm, among other widths that are possible and contemplated herein. In additional or alternative embodiments, the width W6 is in the range of about 5 mm to about 70 mm, among other ranges of widths and/or widths that are possible and contemplated herein. In some embodiments, the width W6 is about 11 mm, among other widths that are possible and contemplated herein.

In some embodiments, the width W5 and the width W6 are the same width or substantially the same width. In other embodiments, the width W6 is greater than the width W5 such that the proximate end 310 is wider than the distal end 308 or, alternatively, the distal end 308 is narrower than the proximate end 310 (e.g., the width W5 is less than the width W6). That is, in various embodiments, the surgical instrument 300 includes a tapered shape and/or tapers from the distal end 308 to the proximate end 310.

A bottom surface 304 may include any suitable shape and/or profile that can facilitate or assist the surgical instrument 300 in performing an osteotomy (e.g., a wedge-shaped osteotomy). In various embodiments, the bottom surface 304 includes a flat or substantially flat surface, among other profiles and/or planes that are possible and contemplated herein.

A top surface 306 may include any suitable profile upon which one or more cutting blades 312 can be positioned. In various embodiments, the top surface 306 includes a slope 318 (see FIG. 3D) that extends upward and/or away from the bottom surface 304 and the distal end 308. The slope 318 may include any suitable grade (e.g., rise over run) that can facilitate and/or assist the surgical instrument 300 in performing an osteotomy and particularly, a wedge-shaped osteotomy. That is, the top surface 306 and/or surgical instrument 300 may include any suitable grade that can facilitate and/or assist the surgical instrument 300 in performing a wedge-shaped osteotomy in one cut and/or one pass.

In various embodiments, the slope 318 includes a grade in the range of about zero degrees (0° or flat, see FIG. 3E) to about fifteen degrees (15°, see FIG. 3D), among other ranges of grades, grades, and/or slopes that are possible and contemplated herein. In other words, an angle θ in the range of about 0° to about 15° (e.g., the angle θ=0°, 1°, 2°, 3°, 4°, 5°, 6°, 7°, 8°, 9°, 10°, 11°, 12°, 13°, 14°, or 15° and/or the angle θ≈0°, 1°, 2°, 3°, 4°, 5°, 6°, 7°, 8°, 9°, 10°, 11°, 12°, 13°, 14°, or 15°) is defined between the top surface 306 and the bottom surface 304 beginning at the distal end 308 and extending upward and toward the proximate end 310, as shown in FIGS. 3D and 3E. In some embodiments, the slope 318 includes a grade of about seven (7°) degrees (e.g., the angle θ=7° or the angle θ≈7°), among other suitable grades and/or slopes that are possible and contemplated herein.

In several embodiments, the top surface 306 includes a set of cutting blades 312 positioned thereon. As illustrated, the set of cutting blades 312 are spaced apart and positioned vertically to form a set of columns of cutting blades 312. As shown, one or more cutting blades 312 are positioned on the top surface 306 so that one end of the cutting blade 312 or cutting blades 312 begin(s) at or substantially at the distal end 308 and extend toward the proximal end 310.

In various embodiments, all of the cutting blades 312 in the set of cutting blades 312 begin at or substantially at the distal end 308 or a portion of the cutting blades 312 in the set of cutting blades 312 begin(s) at or substantially at the distal end 308. The cutting blades 312 may include any suitable shape and/or dimensions at the distal end 308 can assist in and/or facilitate initiating an osteotomy and particularly, a wedge-shaped osteotomy, when oscillated.

A set of cutting blades 312 may include any suitable quantity of cutting blades 312 and/or quantity of columns of cutting blades 312 that can facilitate and/or assist the surgical instrument 300 in performing an osteotomy and particularly, a wedge-shaped osteotomy.

The top surface 306 may include any suitable quantity of cutting blades 312 so that the surgical instrument 300 can perform a wedge-shaped osteotomy in one cut and/or one pass. In various embodiments, the top surface 306 includes a quantity of cutting blades 312 in the range of about 2 cutting blades 312 to about 40 cutting blades 312, among other ranges of quantities of cutting blades 312 and/or quantities of cutting blades 312 that are possible and contemplated herein. In some embodiments, the top surface 306 includes 12 cutting blades 312, among other quantities of cutting blades 312 that are possible and contemplated herein.

While the surgical instrument 300 is shown with a top surface 306 including 14 cutting blades 312, the various embodiments of the surgical instrument 300 are not limited to 14 cutting blades 312. That is, various other embodiments of a surgical instrument 300 can include a different quantity of cutting blades 312 such that the top surface 306 can include a greater quantity of cutting blades 312 than 14 cutting blades 312 or a smaller quantity of cutting blades 312 than 14 cutting blades 312.

Figure 3A:
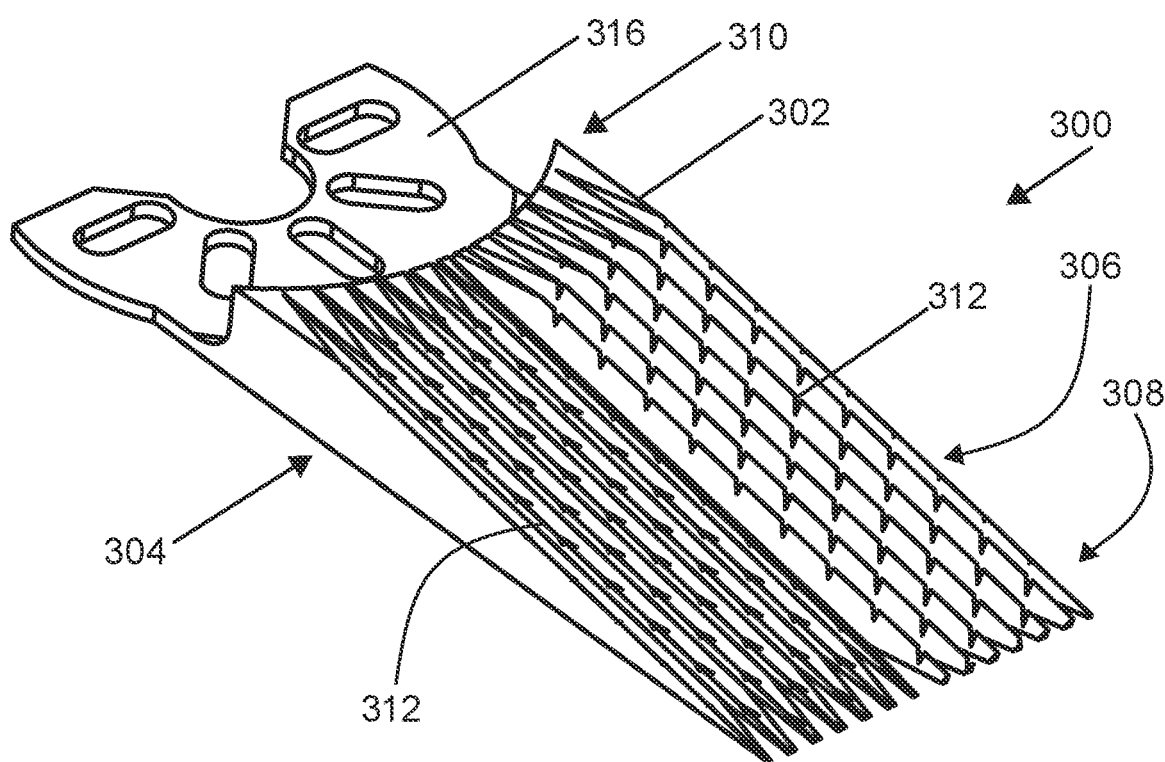
FIG. 3A is a schematic diagram illustrating an overall view of another embodiment of a surgical instrument including multiple columns of cutting blades.
Figure 3B:
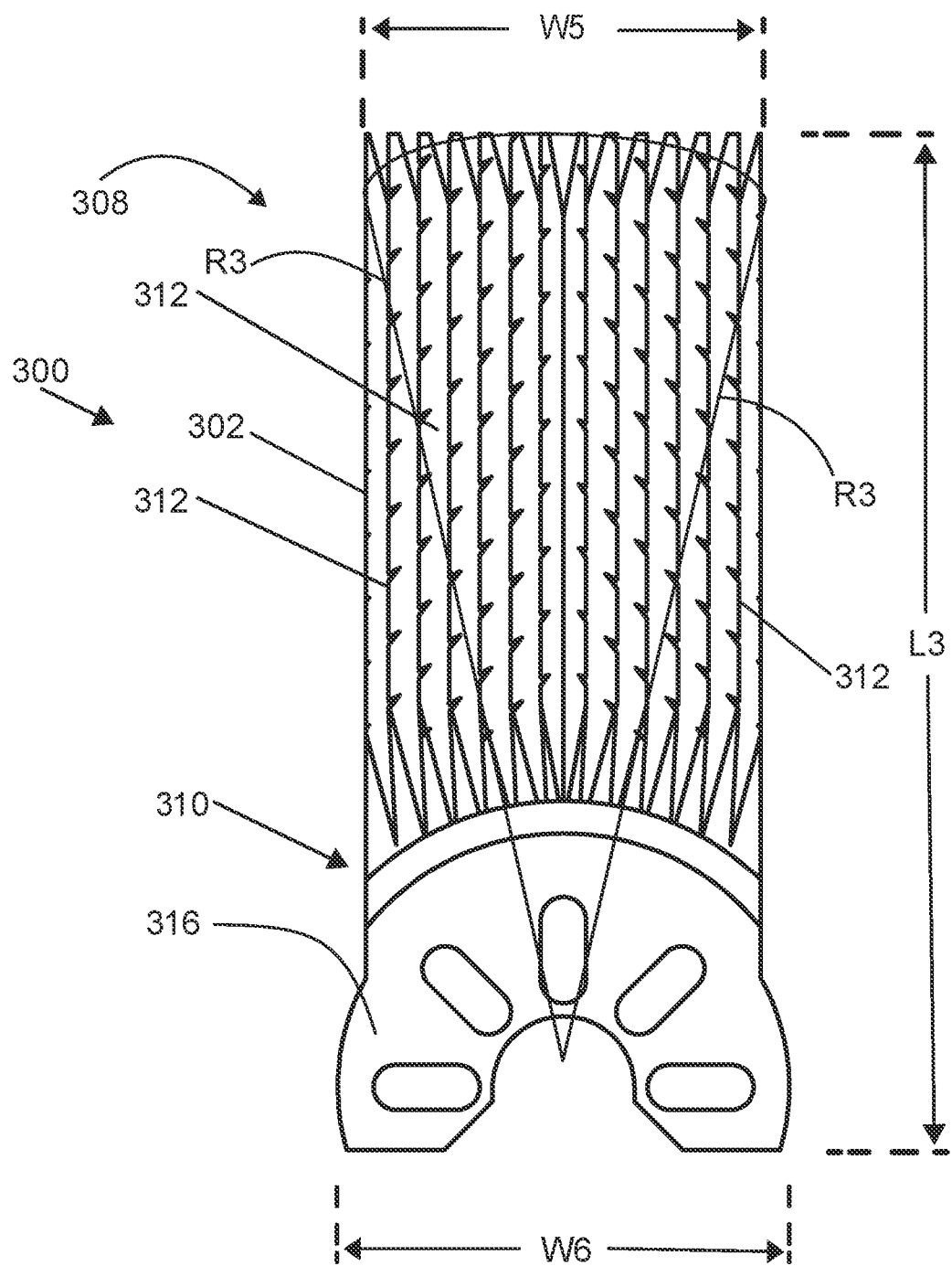
FIG. 3B is a schematic diagram illustrating a top view of the embodiment of a surgical instrument illustrated in FIG. 3A.
Figure 3C:
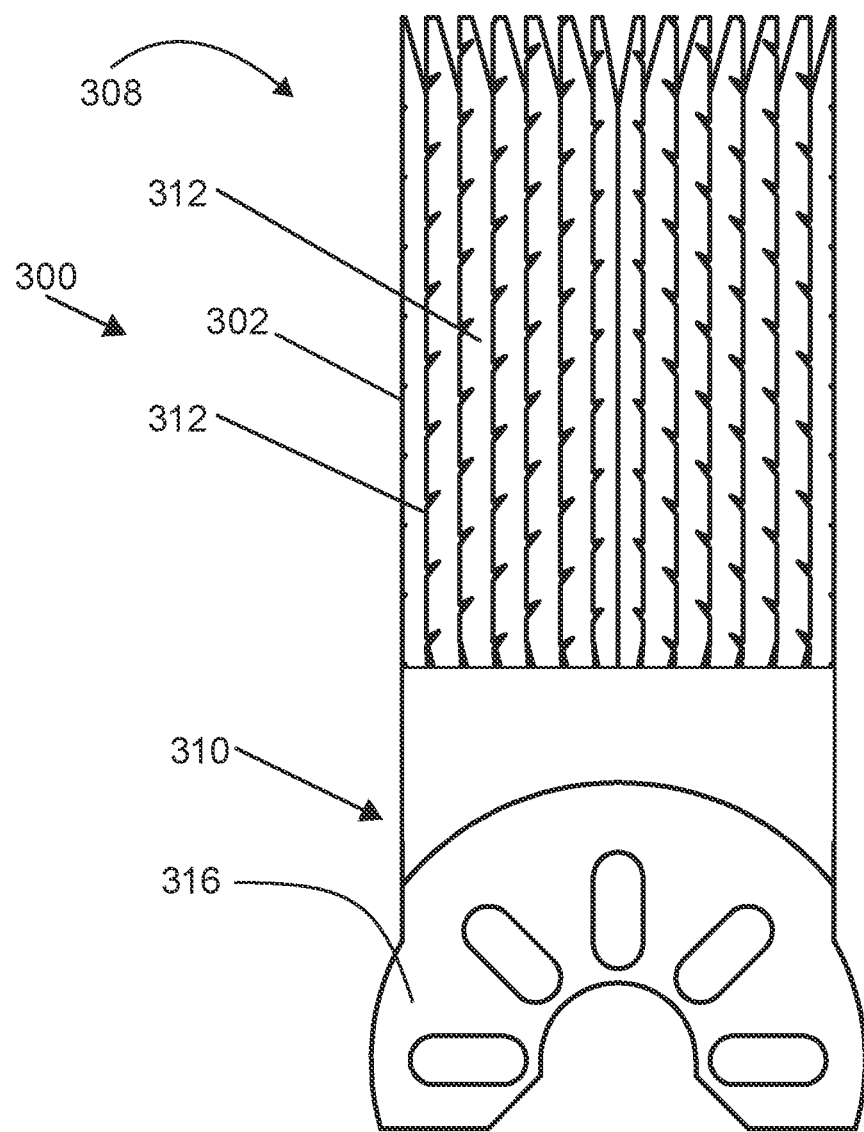
FIG. 3C is a schematic diagram illustrating a top view of another embodiment of the surgical instrument illustrated in FIG. 3A.
Figure 3D:
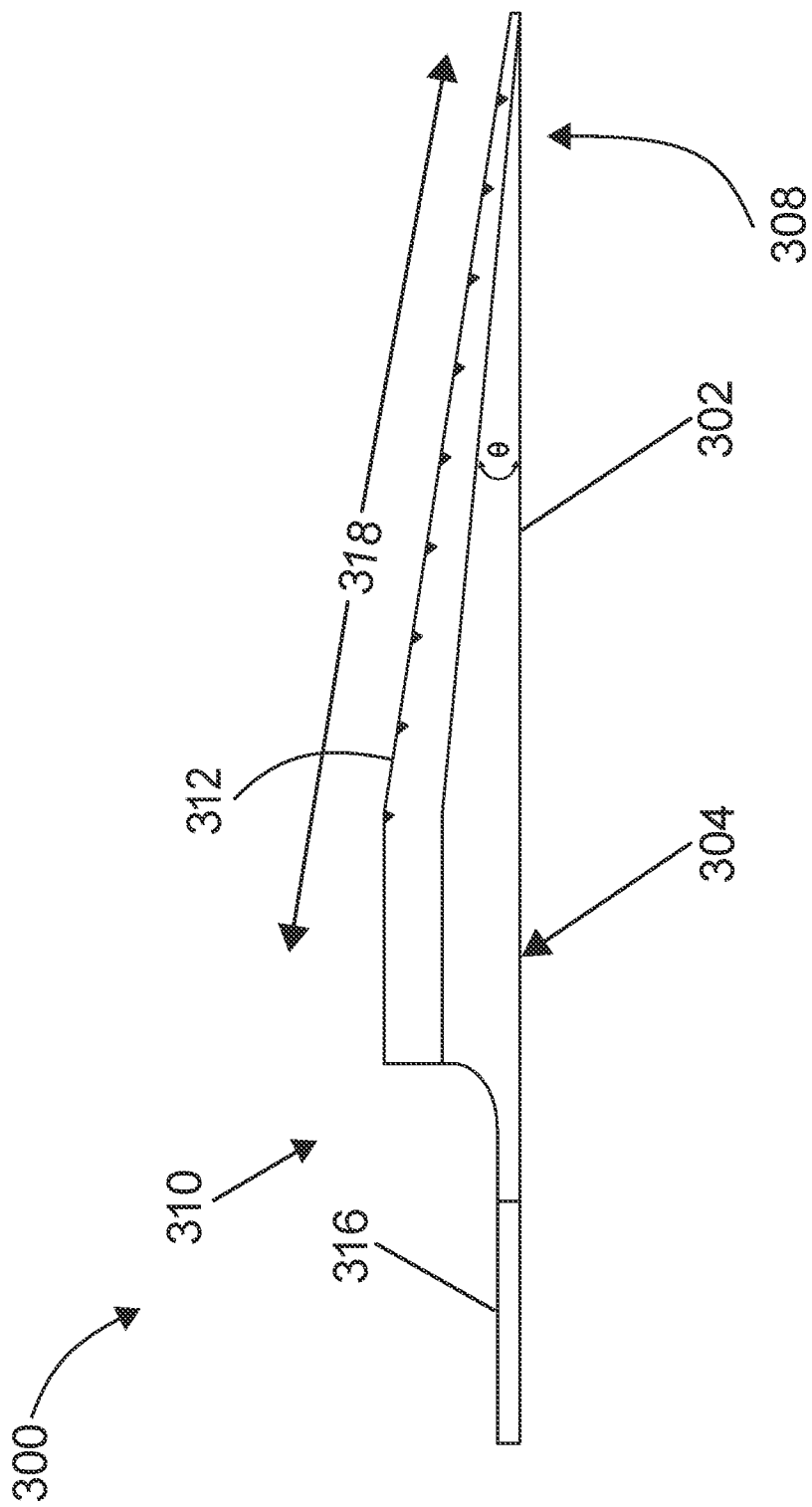
FIG. 3D is a schematic diagram illustrating a side view of the embodiment of a surgical instrument illustrated in FIG. 3A.
Figure 3E:
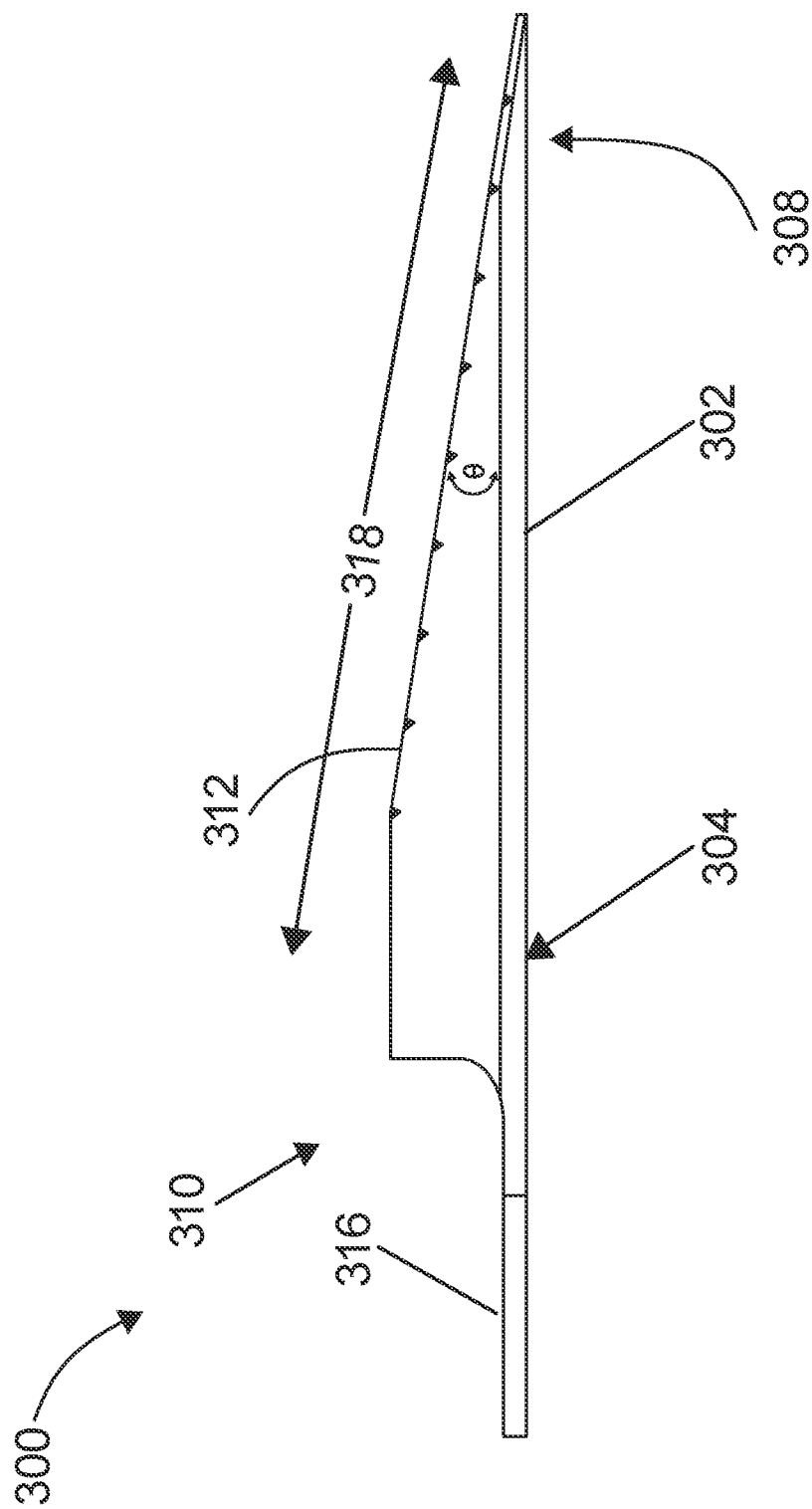
FIG. 3E is a schematic diagram illustrating a side view of the embodiment of a surgical instrument illustrated in FIG. 3A with each row including a gradually greater blade height from a distal end to a proximal end of the surgical instrument.

In some embodiments, the cutting blades 312 may extend over and/or along the entirety or substantially the entirety of the top surface 306 (see FIG. 3B). In other embodiments, the cutting blades 312 extend over and/or along a portion or at least a portion of the top surface 306 (see FIG. 3C). That is, the cutting blades 312 may extend partially or fully from the distal end 308 to the proximal end 310.

The portion of the top surface 306 including the cutting blades 312 may include any suitable sized portion that can produce a wedge-shaped osteotomy. Various embodiments of the surgical instrument 300 may include varying sized portions of the top surface 306 including the cutting blades 312 so that different sized and/or wedge-shaped osteotomies can be obtained. That is, different embodiments may include cutting blades 312 with differing lengths to produce different sized and/or wedge-shaped osteotomies.

A cutting blade 312 may include any suitable shape that can facilitate and/or assist the surgical instrument 300 in performing an osteotomy (e.g., a wedge-shaped osteotomy). In various embodiments, a cutting blade 312 can include a curved blade (e.g., a vertically curved blade), a straight blade, waved blade (e.g., a horizontally curved blade), or a wavy blade (e.g., a blade with multiple horizontal curves), among other suitable shapes that can facilitate cutting bone that are possible and contemplated herein. In additional or alternative embodiments, a cutting blade 312 can include a straight cutting edge and/or a serrated cutting edge, among other cutting edges that are possible and contemplated herein.

In some embodiments, all of the cutting blades 312 in the set of cutting blades 312 on the top surface 306 include the same or substantially the same shape. In alternative embodiments, at least two cutting blades 312 in the set of cutting blades 312 on the top surface 306 include different shapes or substantially different shapes. In one non-limiting example, at least one cutting blade 312 includes a straight blade and at least one cutting blade 312 includes a curved blade (or other non-straight blade), among other shapes and/or combinations of shapes that are possible and contemplated herein. In an additional or alternative non-limiting example, the straight blade(s) and/or the curved blade(s) include a serrated cutting edge.

In additional or alternative embodiments, a set of cutting blades 312 can include at least two subsets of cutting blades 312 in which a first subset includes two or more cutting blades 312 including a first shape and at least a second subset that includes two or more cutting blades 312 including a second, different shape. In some embodiments, one or more of the cutting blades 312 in one or more of the subsets of cutting blades 312 includes a serrated edge.

In further additional or alternative embodiments, the first subset of cutting blades 312 and the second subset of cutting blades 312 include the same quantity of cutting blades 312. In other embodiments, the first subset of cutting blades 312 and the second subset of cutting blades 312 include different quantities of cutting blades 312.

In yet further additional or alternative embodiments, the cutting blades 312 in the first subset of cutting blades 312 and the cutting blades 312 in the second subset of cutting blades 312 can be positioned in a pattern. The pattern may include any suitable pattern that can assist in and/or facilitate performing an osteotomy (e.g., a wedge-shaped osteotomy). In some embodiments, the pattern may include cutting blades 312 with different shapes in an alternating pattern to provide alternating columns of cutting blades 312.

A cutting blade 312 may include any suitable height that can facilitate and/or assist the surgical instrument 300 in performing an osteotomy (e.g., a wedge-shaped osteotomy). In various embodiments, the cutting blades 312 can include a height in the range of about 0.1 mm to about 30 mm, among other suitable heights that can facilitate cutting bone that are possible and contemplated herein. In some embodiments, the cutting blades 312 include a height of about 0.75 mm, among other suitable heights that can facilitate cutting bone that are possible and contemplated herein.

In some embodiments, all of the cutting blades 312 in the set of cutting blades 312 on the top surface 306 include a respective uniform height (see FIG. 3D). In various embodiments, all of the cutting blades 312 in the set of cutting blades 312 include the same respective uniform height or at least two cutting blades 312 in the set of cutting blades 312 include different respective uniform heights.

As shown in FIG. 3D, various embodiments include the body 302 with angle θ created between the bottom surface 304 and the top surface 306 such that the top surface 306 defines the slope 318 from the distal end 308 to the proximal end 310. Further illustrated in FIG. 3D, the set of cutting blades 312 includes a uniform height such that, when positioned on the top surface 306, the cutting surface (or top surface) of each cutting blade 312 mirrors and/or includes the same slope 318 as that of the top surface 306. In other words, the cutting surface of each cutting blade 312 extends vertically and rises upward along the slope 318 from the distal end 308 to the proximal end 310 (see FIG. 3B) or toward the proximal end 310 on a portion of the top surface 306 (see FIG. 3C).

In alternative embodiments, all of the cutting blades 312 on the top surface 306 include a respective height that increases from the distal end 308 to the proximal end 310 (see FIG. 3E). As shown in FIG. 3E, various embodiments include the body with a flat (0° slope) top surface 306 and one or more cutting blades 312 with angle θ between the cutting surface and a surface of the cutting blade 312 positioned on the body 302 such that the height of each cutting blade 312 increases along the slope 318 from the distal end 308 to the proximal end 310.

In various embodiments, the angle θ of each cutting blade 312 is in the range of about 1° to about 15°, among other ranges of angles and/or angles that are possible and contemplated herein. In other words, an angle θ in the range of about 1° to about 15° (e.g., the angle θ=1°, 2°, 3°, 4°, 5°, 6°, 7°, 8°, 9°, 10°, 11°, 12°, 13°, 14°, or 15° and/or the angle θ≈1°, 2°, 3°, 4°, 5°, 6°, 7°, 8°, 9°, 10°, 11°, 12°, 13°, 14°, or 15°) is defined between the cutting surface of each cutting blade 312 and the surface of the cutting blade positioned on the body 302, as shown in FIG. 3E. In other words, the cutting surface of each cutting blade 312 extends vertically and rises upward along the slope 318 from the distal end 308 to the proximal end 310 (see FIG. 3B) or toward the proximal end 310 on a portion of the top surface 306 (see FIG. 3C).

In some embodiments, all of the cutting blades 312 in the set of cutting blades 312 include the same respective increasing height or angle θ such that the cutting blades 312 increase in height starting at or proximate to the distal end 308 and extend to or toward the proximal end 310 at the same rate. In alternative embodiments, at least two cutting blades 312 in the set of cutting blades 312 include different respective increasing heights or angles θ such that at least two cutting blades 312 increase in height starting at or proximate to the distal end 308 and extend to or toward the proximal end 310 at different rates.

In some embodiments, the set of cutting blades 312 are positioned on the distal end 308 in a straight line or substantially straight line. In other embodiments, the set of cutting blades 312 are positioned along a curve on the distal end 308 defined by a radius R3.

The radius R3 may be any suitable radius and/or curvature that can assist in and/or facilitate initiating an osteotomy (e.g., a wedge-shaped osteotomy) when oscillated. In various embodiments, the radius R3 is in the range of about 5 mm to about 80 mm, among other ranges of lengths and/or lengths that can define an amount and/or degree of curvature that are possible and contemplated herein. In some embodiments, the radius R3 is about 25 mm, among other lengths that can define an amount and/or degree of curvature that are possible and contemplated herein.

In some embodiments, the cutting blades 312 include a cutting surface along the slope 318 that can define single-plane. The single-plane may define a cutting slope 318 that can perform a wedge-shaped osteotomy in a single cut and/or single pass.

As further shown in FIGS. 3A through 3E, the proximal end 310 includes an attachment mechanism 316 positioned thereon. The attachment mechanism 316 may include any suitable size dimensions, shape, and/or configuration that enables attachments of the surgical instrument 300 to a surgical instrument (not shown). That is, while the attachment mechanism 316 is shown as including particular relative size dimensions, shapes, and configurations, the various embodiments of the surgical instrument 300 are not limited to the illustrated attachment mechanism 316. That is, other embodiments of the surgical instrument 300 may include one or more different relative size dimension(s), shapes, and/or configurations.

The various embodiments discussed herein may be practiced in other specific forms and the described embodiments are to be considered in all respects only as illustrative, and not restrictive. The scope of the technology is, therefore, indicated by the appended claims rather than by the foregoing description. All changes that come within the meaning and range of equivalency of the claims are to be embraced within their scope. That is, one of ordinary skill in the art will appreciate that modifications and/or adaptations to the various aspects may be made without departing from the scope of the present technology, as set forth in the following claims.

The invention claimed is:

1. A surgical instrument, comprising:
a body comprising a distal end, a proximal end, a bottom surface, and a top surface;
an attachment mechanism positioned on the proximal end; and
a plurality of cutting blades spaced apart and positioned on the top surface in columns of cutting blades,
wherein:
the top surface includes a flat plane;
each cutting blade in the plurality of columns of cutting blades comprises a cutting portion extending away from the top surface;
the plurality of columns of cutting blades extend along at least a portion of the top surface from the distal end to the proximal end; and
each cutting blade in the plurality of columns of cutting blades comprises a same height.

2. The surgical instrument of claim 1, wherein:
the distal end includes a first horizontal width;
the proximal end includes a second horizontal width; and
the first horizontal width is greater than the second horizontal width such that the body includes a width that tapers from the distal end to the proximal end.

3. The surgical instrument of claim 1, wherein:
the proximal end and the distal end include a same horizontal width such that the body includes a uniform width.

4. The surgical instrument of claim 1, wherein:
the plurality of cutting blades includes a quantity of cutting blades in the range of two cutting blades to 40 cutting blades.

5. The surgical instrument of claim 1, wherein:
the distal end includes a first horizontal width;
the proximal end includes a second horizontal width; and
the first horizontal width is less than the second horizontal width such that the body includes a width that tapers from the proximal end to the distal end.

6. The surgical instrument of claim 2, wherein:
the plurality of cutting blades includes a quantity of cutting blades in the range of two cutting blades to 40 cutting blades.

7. The surgical instrument of claim 3, wherein:
the plurality of cutting blades includes a quantity of cutting blades in the range of two cutting blades to 40 cutting blades.

8. A surgical instrument, comprising:
a body comprising a distal end, a proximal end, a bottom surface, and a top surface, the top surface including a slope extending upward and along a single plane from the distal end to the proximal end; and
a plurality of cutting blades spaced apart and positioned on the top surface in columns of cutting blades,
wherein:
each of the plurality of cutting blades comprises a cutting portion extending away from the top surface;
each of the plurality of cutting blades extends along at least a portion of the top surface, and
the plurality of cutting blades comprises a uniform height.

9. The surgical instrument of claim 8, wherein:
the slope defines an angle between the top surface and the bottom surface in the range of 1 degree and 15 degrees.

10. The surgical instrument of claim 8, wherein:
each cutting blade in the plurality of cutting blades comprises a respective uniform height.

11. The surgical instrument of claim 10, wherein:
each cutting blade in the plurality of cutting blades comprises a same respective uniform height.

12. The surgical instrument of claim 8, wherein:
the distal end includes a first horizontal width;
the proximal end includes a second horizontal width; and
the first horizontal width is greater than the second horizontal width such that the body includes a width that tapers from the distal end to the proximal end.

13. The surgical instrument of claim 8, wherein:
the proximal end and the distal end include a same horizontal width such that the body includes a uniform width.

14. The surgical instrument of claim 8, wherein:
the plurality of cutting blades includes a quantity of cutting blades in the range of two cutting blades to 40 cutting blades.

15. A surgical instrument, comprising:
a body comprising a distal end, a proximal end, a bottom surface, and a top surface; and
a plurality of cutting blades spaced apart and positioned on the top surface in columns of cutting blades,
wherein:
each of the plurality of cutting blades extends vertically along the portion of the top surface, and
each cutting blade in the plurality of cutting blades comprises a respective increasing height extending from the distal end to the proximal end such that a first height toward the proximal end is greater than a second height at the distal end of each cutting blade.

16. The surgical instrument of claim 15, wherein:
the top surface is flat or includes a slope; and
each cutting blade in the plurality of cutting blades comprises a same respective increasing height.

17. The surgical instrument of claim 15, wherein:
the top surface is flat or includes a slope; and
each cutting blade in the plurality of cutting blades comprises a same respective uniform height.

18. The surgical instrument of claim 15, wherein:
the top surface is flat or includes a slope; and
at least two cutting blades in the plurality of cutting blades comprise different respective increasing heights.

19. The surgical instrument of claim 15, wherein:
the top surface is flat or includes a slope; and
at least two cutting blades in the plurality of cutting blades comprise different respective uniform heights.

20. The surgical instrument of claim 15, wherein:
the distal end includes a first horizontal width;
the proximal end includes a second horizontal width;
the plurality of cutting blades includes a quantity of cutting blades in the range of two cutting blades to 40 cutting blades; and
one of:
   the first horizontal width is greater than the second horizontal width such that the body includes a width that tapers from the distal end to the proximal end, or
   the proximal end and the distal end include a same horizontal width such that the body includes a uniform width.

\* \* \* \* \*